(12) United States Patent
Kaack et al.

(10) Patent No.: US 7,728,586 B2
(45) Date of Patent: Jun. 1, 2010

(54) METHOD AND DEVICE FOR TESTING PIPES IN A NON-DESTRUCTIVE MANNER

(75) Inventors: Michael Kaack, Bochum (DE); Stefan Nitsche, Mülheim (DE); Thomas Orth, Mülheim (DE)

(73) Assignee: V & M Deutschland GmbH, Dusseldorf (DE)

(*) Notice: Subject to any disclaimer, the term of this patent is extended or adjusted under 35 U.S.C. 154(b) by 649 days.

(21) Appl. No.: 11/631,743

(22) PCT Filed: Jun. 10, 2005

(86) PCT No.: PCT/DE2005/001074

§ 371 (c)(1),
(2), (4) Date: Jan. 5, 2007

(87) PCT Pub. No.: WO2006/007807

PCT Pub. Date: Jan. 26, 2006

(65) Prior Publication Data

US 2008/0042645 A1    Feb. 21, 2008

(30) Foreign Application Priority Data

Jul. 16, 2004    (DE)    ........................ 10 2004 035 174

(51) Int. Cl.
*G01N 27/82* (2006.01)
*G01R 33/12* (2006.01)
(52) U.S. Cl. ........................ 324/242; 324/227; 324/232
(58) Field of Classification Search .................. 324/242, 324/227, 232
See application file for complete search history.

(56) References Cited

U.S. PATENT DOCUMENTS

| 6,366,085 B1 | 4/2002 | Yeshurun et al. |
| 2003/0117134 A1 | 6/2003 | Almaguer |

FOREIGN PATENT DOCUMENTS

| DE | 2925924 | 1/1981 |
| JP | 62185162 | 8/1987 |
| WO | WO02095383 | 11/2002 |

OTHER PUBLICATIONS

International Search Report for corresponding International Appln, No. PCT/De2005/001074 completed Sep. 2, 2005. (Mailed: Oct. 6, 2005).

*Primary Examiner*—Reena Aurora
(74) *Attorney, Agent, or Firm*—Duane Morris LLP

(57) ABSTRACT

The present invention pertains to a method for the nondestructive testing of pipes made of ferromagnetic steel by means of a stray flux, in which the pipe, which is moving in the longitudinal direction and alternatively additionally rotating, is magnetized by a constant field, and the generated magnetic flux is transmitted into the pipe in a contactless manner, and the flaws that are located in the near-surface area of the outer or inner surface of the pipe bring about magnetic stray fluxes, which emerge from the pipe surface and are detected by means of sensors. The amplitudes, preferably of the horizontal field component of the magnetic stray flux, which vary in the vertical direction, are detected, on the one hand, at a near-surface distance from the pipe outer surface, and, on the other hand, at a distance lying further remotely therefrom, and the detected signals are related to one another.

13 Claims, 5 Drawing Sheets

Figure 3A:
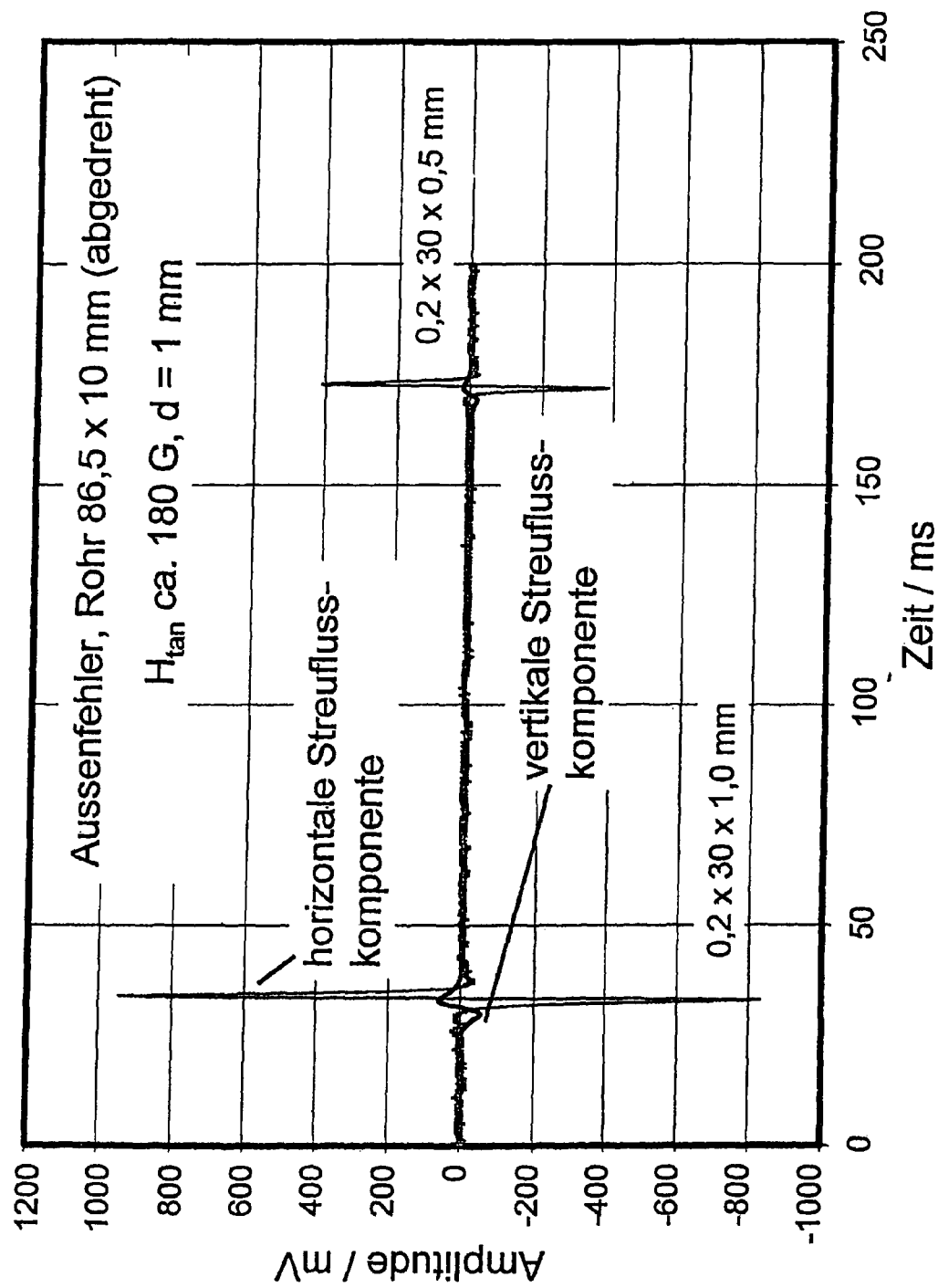

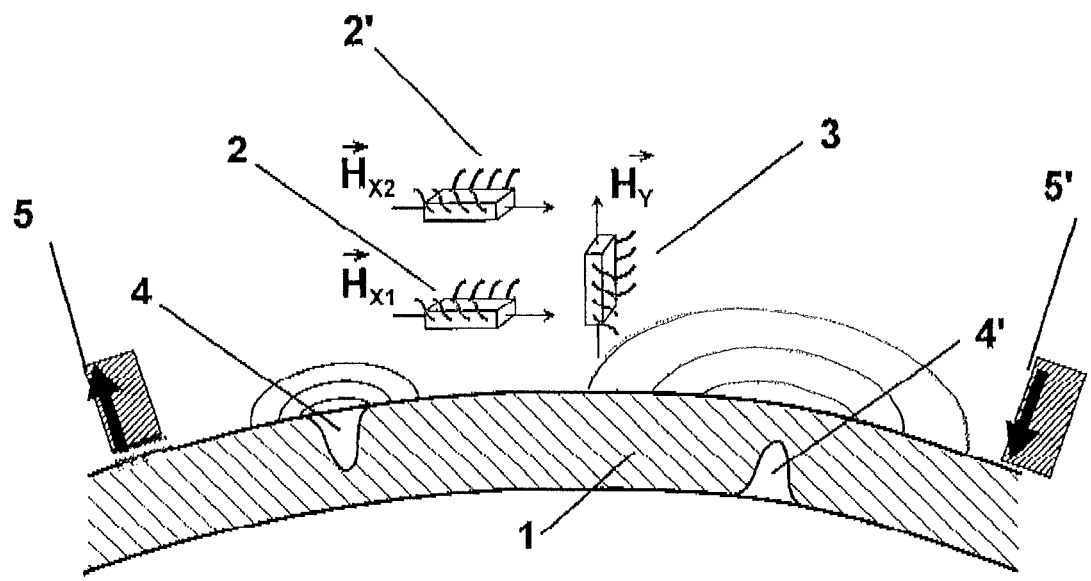
Figur 1a
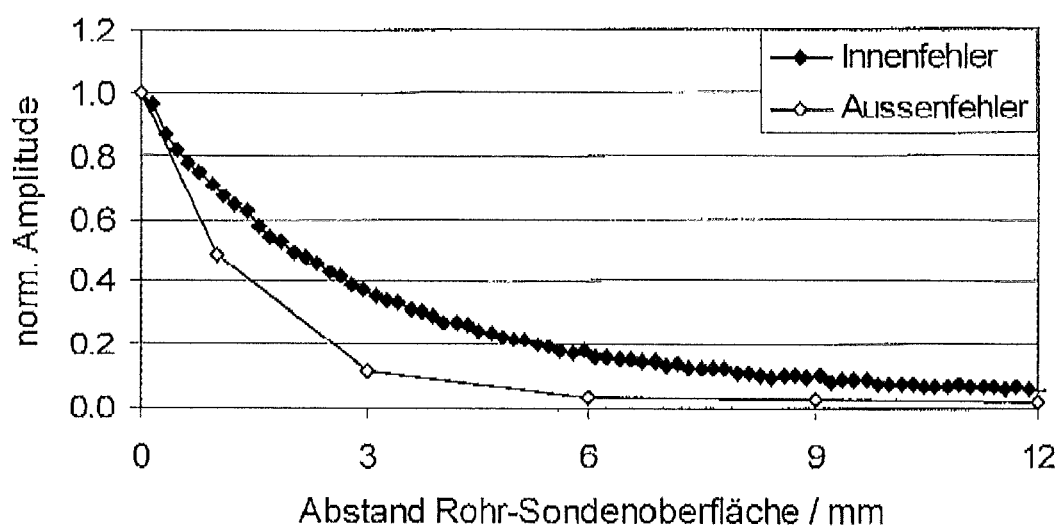
Figur 1b

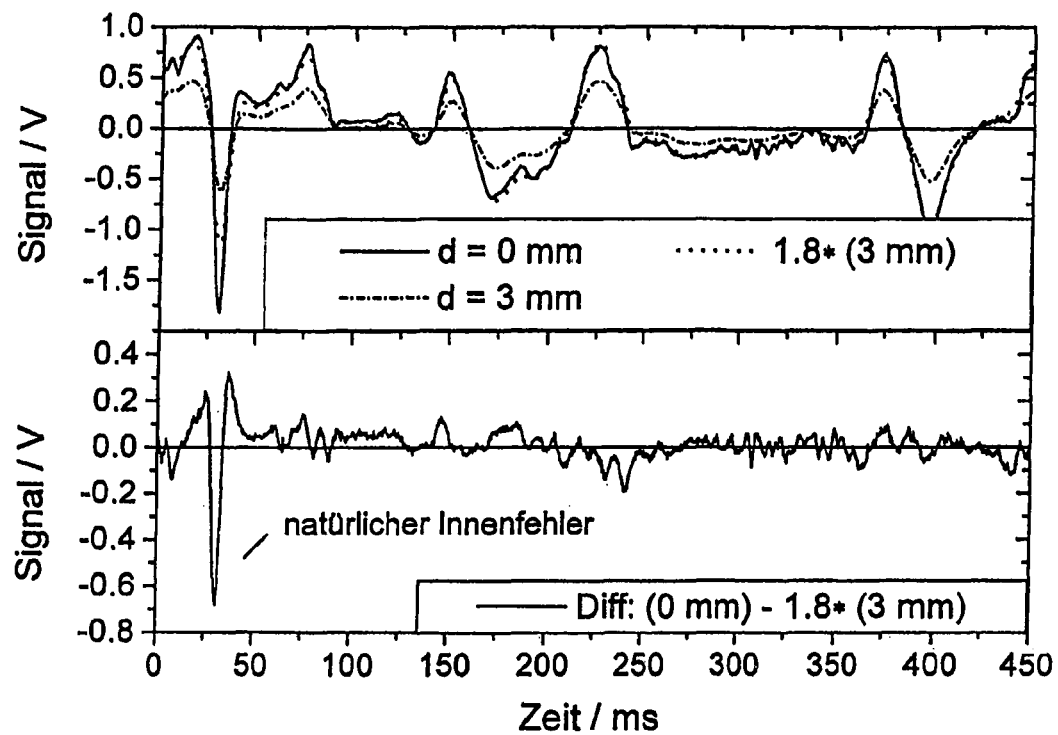
Figur 2a
KEY:
natürlicher Innenfehler = natural internal defect
Zeit / ms = Time / msec.

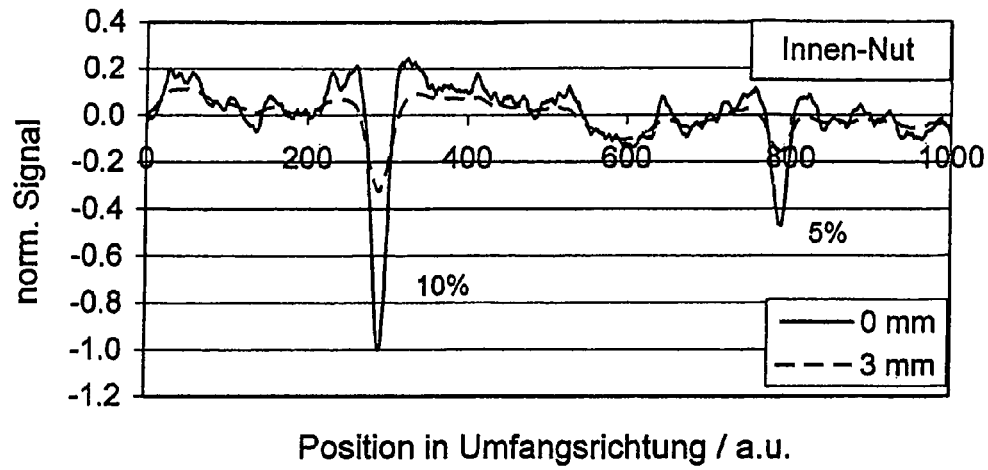
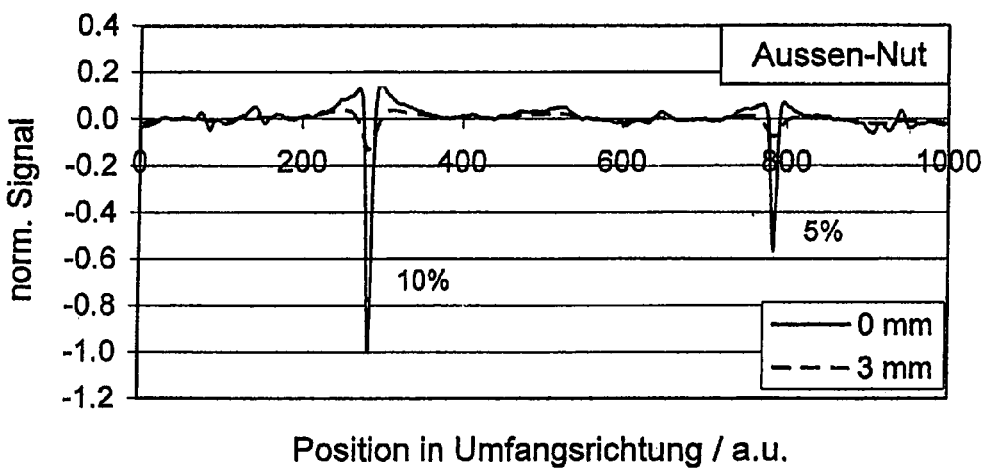
Figur 2b
KEY:
Innen-Nut = Internal groove
Position in Umfangsrichtung / a.u. = Position in circumferential direction / a.u. [Angstrom units? - Tr.Ed.]
Aussen-Nut = External groove
Verhältnis = Ratio
~0,30 für Innen-Nut = ~ 0.30 for internal groove
~0.15 für Aussen-Nut = ~ 0.15 for external groove
unabhängig von der Tiefe = regardless of the depth KEY:
Aussenfehler, Rohr 86,5 x 10 mm (abgedreht) = External defect, pipe 86.5 x 10 mm (faced)
horizontale Streuflusskomponente = horizontal stray flux component
vertikale Streuflusskomponente = vertical stray flux component
Zeit / ms = Time / msec KEY:
horizontale Streuflusskomponente = horizontal stray flux component
10% Innen-Nut, Rohr 86,5 x 10 mm (abgedreht) = 10% internal groove, pipe 86.5 x 10 mm (faced)
vertikale Streuflusskomponente = vertical stray flux component
Zeit / ms = Time / msec

METHOD AND DEVICE FOR TESTING PIPES IN A NON-DESTRUCTIVE MANNER

The present invention pertains to a method for the nondestructive testing of pipes made of ferromagnetic steel by means of a stray flux according to the preamble of patent claim 13.

The prior-art stray flux testing is applied in pipes made of ferromagnetic steel in order to detect, in particular, longitudinally aligned, near-surface flaws, e.g., cracks, which cannot be detected in a cost- and time-intensive manner by another testing method or only with high inaccuracy.

E.g., cracks, which extend at least ca. 0.3 mm starting from the surface of the pipe, are detected with this method (Nondestructive Evaluation, A Tool in Design, Manufacturing, and Service, CRC Press 1997).

Constant field magnetization is used in the measuring method known according to the state of the art for the detection of near-surface defects on the inside or outside of pipes.

In contrast to the alternating field magnetization used, e.g., in bars, which only permits a detection of external defects, defects on the inner surface of pipes can also be detected with the constant field magnetization.

In the stray flux testing with constant field magnetization the effect is utilized that the induction flux density rises in the area of a defect, whereby the magnetic field lines are disturbed by external or internal defects in their otherwise linear expansion, such that a so-called stray flux is formed. This stray flux, which emerges on the pipe surface, is used for the detection of defects.

The magnetic stray flux density is usually measured with Hall probes or induction coils, which are arranged in a test head. When using induction coils (arranged fixed about the [sic, "dass" is an obvious typo for "das"—Tr.Ed.] pipe), it is necessary for testing the entire pipe surface in the pipe longitudinal axis that the pipe rotates and moves in the longitudinal direction of the pipe. On the other hand, Hall probes can also be used in case of a pipe moving only in the longitudinal direction of the pipe. The processed signals can then be used for sorting and marking the pipes and the test results can be recorded.

With this prior-art surface testing method, possible flaws on the pipe surface can be recognized in a reliable manner, an assignment of the defect signals to the outer surface or inner surface of the pipe, i.e., a separation of defects, is not possible with this method or only in a very complicated manner.

According to operating investigations, even a frequency analysis of the signals measured with Hall probes or induction coils is not sufficient for an accurate assignment of defects, since the measured frequencies lie close to one another and are additionally superimposed by a type of "background noise." This absolutely coherent background signal may have various causes, e.g., wall thickness variations caused by rolling.

For this reason, an attempt is usually made to minimize this background signal via a local subtraction of the measured signals by at least two single probes lying in the same plane. However, this has the drawback that, depending on the size or length of the defect, there is an insensitivity to defects exactly in the direction of the local subtraction. This represents a problem particularly in natural defects, which may not be sharply defined, but rather run in or run out without contrast.

For this reason, according to WO 021095383 A2, an attempt is made to minimize this background signal via a local subtraction of the measured signals by at least two single probes lying in the same plane. However, this has the drawback that, depending on the size or length of the defect, there is an insensitivity to defects that lie exactly in the direction of the local subtraction. This represents a problem particularly in natural defects, which may not be sharply defined, but rather run in or run out without contrast.

The amplitudes of the stray fluxes on the pipe outer surface caused by internal defects are markedly lower in comparable defect dimensions than those that are produced by defects on the outer surface of the pipe. Therefore, for the reliable recognition of defects, the sensitivity of Hall probes or induction coils to possible internal defects is used in the prior-art method. However, this has the disadvantageous effect that external defects that can possibly be tolerated are still detected in a too sensitive manner and are displayed, which leads to unnecessary rejection or reworking of the pipes.

Detecting the angular position or the shape of a defect extending from a workpiece surface into the interior by means of stray flux testing has become known from JP 62185162 A. Herein, amplitude signals are generally detected by two sensors placed at a vertical distance from one another, evaluated, related to one another, and an indicator of the shape or angular position of the defect is derived from the relationship. There is no indication as to how a separation of external and internal defects can be achieved in the stray flux testing of a pipe.

A separation of defects according to pipe outer surface or inner surface defects is therefore desirable for many reasons. In addition, defects which lie on the outer or inner surface of the pipe may have different causes, which come, for example, from the preceding production steps in the production of the pipe (defective internal tool or roller) or from defects in the starting material. An early fault localization and fault recognition and corrective measures resulting therefrom is [sic, are?—Tr.Ed.] made difficult and likewise leads [sic, lead?—Tr.Ed.] to unnecessarily high failure and reworking rates. Depending on the pipe diameter, reworking can no longer be done at all in defects on the pipe inner surface, so that these pipes have to be sorted out as rejects at any rate.

The object of the present invention is to provide a reliable and cost-effective method and device for the nondestructive testing of pipes made of ferromagnetic steel by means of a stray flux, with which a clear assignment of defects to the outer or inner surface of the pipe is possible.

According to the present invention, this object is accomplished in that the amplitude, preferably of the horizontal field component of the magnetic stray flux, which varies in the vertical direction, is detected by means of magnetic-field-sensitive scanning probes, on the one hand, at a near-surface distance from the pipe outer surface and, on the other hand, at a distance lying further remotely therefrom, and the detected signals are related to one another.

Advantageously, the near-surface distance of the scanning probes from the pipe outer surface is ca. 0.5 mm to 1.5 mm in order to avoid damages to the probe because of variations in the diameter of the pipe. A distance of ca. 1 mm has proven to be particularly favorable. According to the present invention, the second probe is located at a distance of ca. 2-5 mm from the first probe, whereby a distance of ca. 3 mm is considered to be particularly advantageous.

The method according to the present invention is based on the discovery that the stray flux amplitude of the horizontal field component caused by defects on the pipe outer surface drops off very quickly with increasing vertical distance from the pipe outer surface and the stray flux amplitude on the pipe outer surface [caused] by defects on the pipe inner surface drop off markedly more weakly. Studies have shown that the drop off of the amplitude of an external defect is approximately always twice as great as the amplitude drop-off of a defect lying on the pipe inner surface.

The measured signals are superimposed by background signals ("background noise"), which are caused by local variations in diameter, for example, due to wall thickness variations or adhesions of scale on the pipe outer surface.

According to the present invention, therefore, the amplitude signals measured at the different distances to the pipe outer surface are related, whereby advantageously defects can now likewise be assigned to the outer or inner surface besides the extensive noise suppression.

Hereby, at first the amplitude of the (weaker) signal detected at the further remotely lying distance is advantageously increased by a factor of >1, and preferably 1-2, and then related to the amplitude of the signal detected in the near-surface area via a subtraction.

The advantage of this method of proceeding is that the background noise is now filtered out of the measured signal, such that only the pure defect signal is still displayed, which can now be assigned to an external or internal defect because of the different gradients. Consequently, the drawbacks of the prior-art evaluation method by means of subtraction of signals of the sensors lying in one plane are likewise advantageously avoided.

The prerequisite for using this method, and in particular relating both signal portions of the measurements from the various height distances to the pipe outer surface to one another, is the use of highly sensitive magnetic field sensors, which also still supply clearly assignable stray flux signals with evaluable signal/noise ratio at remarkable distances from the pipe outer surface (for example, 5 mm).

Since Hall probes or induction coils can detect stray fluxes only at a very near-surface distance of up to ca. 2 mm because of the noise effect, these detectors are not optimal for the method according to the present invention or are not at all suitable for measuring at greater distances from the test surface.

According to the present invention, therefore, so-called GMR (giant magnetoresistance) sensors are used for the proposed test method, which have a high field sensitivity and a high insensitivity to electrical disturbance variables in the low-band spectrum and therefore can also be used at a greater distance to the test surface in comparison to the known Hall probes or induction coils.

As an alternative, however, the known Hall probes or induction coils may also be used for the near-surface-positioned sensors, and GMR sensors may be used for the probes arranged further from the pipe outer surface.

In an advantageous embodiment of the method according to the present invention, the vertical field component of the stray flux is likewise detected for further improvement in the defect recognition and assignment and related to the amplitude of the horizontal field component or components of the stray flux.

Studies have shown that the horizontal field signals (amplitude, gradient) of an external defect differ markedly from its vertical field signal (amplitude, gradient). On the other hand, a comparable order of magnitude is used for the horizontal or vertical field signal in case of an internal defect.

According to the present invention, a further improved separation of defects is now possible by means of a combined detection and evaluation of the measured vertical and horizontal field amplitudes. To this end, the determined amplitudes for the horizontal and vertical fields are each related separately for external and internal defects.

For example, signal ratios of ca. 10 for an external defect and of ca. 1 for an internal defect were determined in tests. This means that the signals of an external defect are displayed ca. 10 times stronger than those of an internal defect, such that a very accurate separation of pipe external or internal defects is made possible with this method.

Figure 3B:
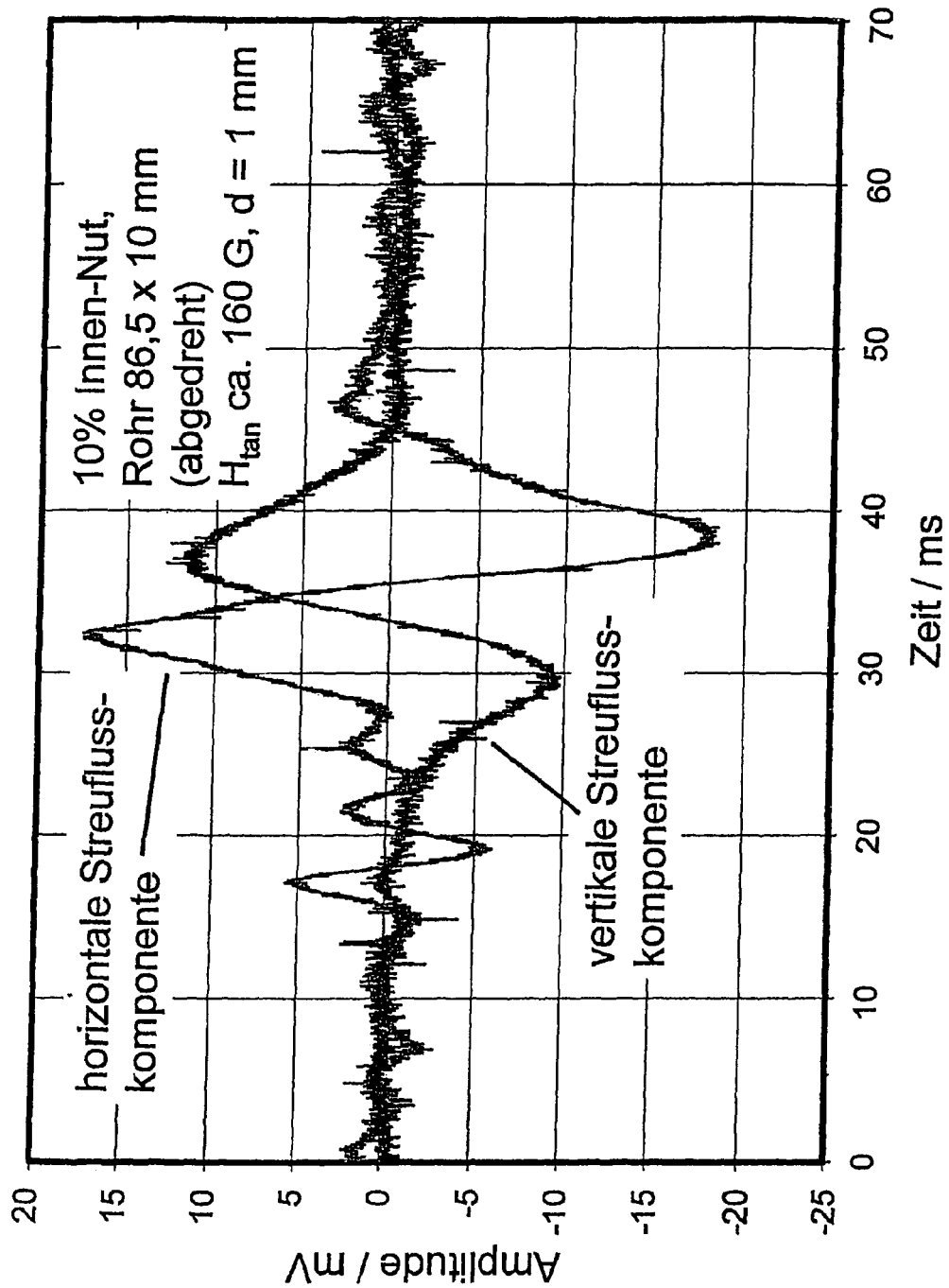

The present invention is explained in detail below on the basis of the figures. The same reference numbers in the different figures designate the same components. In the drawings:

FIG. 1a schematically shows the illustrated testing device according to the present invention, FIG. 1b shows the signal course of horizontal field amplitudes at various distances from the test surface (schematically), FIG. 2a shows signal localization by means of subtraction, FIG. 2b shows assignment of defects based on different amplitude gradients, FIG. 3a shows defect signals of external defects, and FIG. 3b shows defect signals of internal defects.

FIG. 1a shows in a schematic view the testing device according to the present invention for the nondestructive testing of pipes made of ferromagnetic steel by means of a stray flux.

A pipe 1 to be tested, which has a defect 4 lying on the pipe outer surface and a defect 4' lying on the pipe inner surface, is shown. The testing device consists of two scanning probes 2 and 2' for detecting the amplitudes of the horizontal field component of the magnetic stray flux H.sub.x which vary in the vertical direction. The magnetization yoke 5-5' for the contactless production of the magnetic flux is shown here.

The first scanning probe 2 is located at a close distance of ca. 1 mm from the surface of the pipe 1, which is arranged in a testing device not shown in detail. A second scanning probe 2' is arranged in the testing device above the scanning probe 2 at a distance of ca. 3 mm from the first probe. A further scanning probe 3 is arranged vertically to the scanning probes 2, 2' for the detection of the vertical field component of the magnetic stray flux $H_y$. Advantageously, all the scanning probes are embodied as so-called GMR sensors.

FIG. 1b shows a schematic course of the measured signals of the horizontal field amplitudes measured at the various distances from the test surface. It is obvious that the amplitude signals of an internal defect fall off markedly more weakly with increasing distance from the test surface than those of an external defect. For example, the gradient for an internal defect is determined at a value of ca. 0.3 and for an external defect at a value of ca. 0.15. The determined values for the amplitude ratios are thus approximately twice as great for an external defect as for an internal defect, such that a clear assignment of defects is possible.

FIG. 2a shows, in the upper part of the graph, the course of the amplitude signal for a measurement, whereby the defects are assigned by means of boosting and subtraction. Hereby, at first, to suppress the "background noise," the signal measured at a greater distance from the pipe outer surface is boosted, for example, with a factor of 1.8 and then subtracted from the signal measured at a lesser distance.

The lower part of FIG. 2a shows the difference signal, whereby a defect signal can clearly be verified on the left edge of this view.

FIG. 2b shows typical defect signals of such flattened signal courses for artificially produced defects (grooves) on the pipe outer or inner surface. In the case of a defect lying on the pipe inner surface, the amplitude ratio is ca. 0.3 for the different measured distances and ca. 0.15 for external defects, such that the defects now clearly can be assigned to the pipe outer or inner surface.

For the further optimization of the signal evaluation and thus of the separation of defects, as shown in FIG. 3, the measured signal of the vertical field component may additionally be evaluated.

FIG. 3a shows the typical defect signals for a 1-mm or 0.5-mm-deep external defect, and FIG. 3b for a 1-mm-deep internal defect. The signal for the horizontal field component and for the vertical field component each is plotted herein.

In the left area of the graph, FIG. 3a shows the defect signal of a 1-mm-deep defect. The horizontal field component of the stray flux is ca. 10 times greater than the corresponding vertical amplitude, so that this defect can be identified as an external defect. The same conditions can be determined for other defect depths as well. In the right area of the graph, the defect signal of a 0.5-mm-deep defect is shown. The horizontal field component of the stray flux is also ca. 10 times greater here than the vertical field component.

FIG. 3b shows the typical signal course of an artificially produced internal defect (groove). If the amplitude of the magnetic stray flux lying in the horizontal direction is related to the amplitude lying in the vertical direction, then a ratio of ca. 1 results for the internal defect. This means that it is possible to identify, clearly and with great certainty, external and internal defects via the ratio determination of the signals measured and processed according to the present invention and thus it is made possible to assign defects to the pipe external or internal defects.

LIST OF REFERENCE NUMBERS

| No. | Designation |
| --- | --- |
| 1 | Pipe |
| 2, 2' | Scanning probes for vertical field |
| 3 | Scanning probe for horizontal field |
| 4, 4' | External/internal defects |
| $H_x$ | Horizontal field component of the magnetic stray flux |
| $H_y$ | Vertical field component of the magnetic stray flux |

The invention claimed is:

1. A method for non-destructive testing of a pipe made of ferromagnetic steel comprising
   a stray flux; and
   a pipe, wherein the pipe moves in a longitudinal direction and alternatively additionally rotates, and is magnetized by a constant field; and
   a generated magnetic flux, which is transmitted into the pipe in a contact-free manner, and flaws that are located in a near-surface area of an outer or inner surface of the pipe bring about at least one magnetic stray flux that is detected by sensors; wherein
   at least a horizontal field component of the magnetic stray flux, comprising both a horizontal field component and a vertical field component, is detected, whereby its amplitude, which varies in a vertical direction to the pipe surface, is detected at a near-surface distance from the pipe outer surface and a distance lying further remotely therefrom, and the detected signals are related to one another.

2. The method of claim 1, wherein the near-surface distance is about 0.5 to 1.5 mm.

3. The method of claim 2, wherein the distance lying further remotely from the pipe outer surface is about 2 to 5 mm.

4. The method of claim 1, wherein the distance lying further remotely from the pipe outer surface is about 2 to 5 mm.

5. The method of claim 1, wherein the amplitude of the signal detected at the distance lying further remotely from the pipe outer surface is increased by a factor >1 and is subtracted from the amplitude of the signal detected at the near-surface area.

6. The method of any one of claims 1-3, wherein the amplitude of the vertical field component of the magnetic stray flux is additionally detected and is related to the amplitude of the said horizontal field component.

7. A device for non-destructive testing of a pipe made of ferromagnetic steel comprising
   a magnetic stray flux; and
   a pipe, wherein the pipe moves in a longitudinal direction and alternatively additionally rotates; and
   a magnetization yoke, which transmits a magnetic flow into the pipe in a contact-free manner; and
   magnetic-field-sensitive scanning probes for detecting an amplitude varying in a vertical direction to a pipe surface by means of a horizontal field component of the magnetic stray flux, wherein the magnetic stray flux can be split into the horizontal field component and a vertical field component; and
   an evaluation unit,
   wherein the magnetic-field-sensitive scanning probes are arranged at a near-surface distance from the pipe outer surface and at a distance lying further remotely therefrom.

8. The device of claim 7, wherein at the near-surface distance the scanning probes are embodied as Hall probes, and at the distance lying further remotely from the pipe outer surface, the scanning probes are embodied as giant magnetoresistance sensors.

9. The device of claim 7, wherein at the near-surface distance the scanning probes are embodied as induction coils, and at the distance lying further remotely from the pipe outer surface, the scanning probes are embodied as giant magnetoresistance sensors.

10. The device of claim 7, wherein at the near-surface distance the scanning probes are embodied as giant magnetoresistance sensors, and at the distance lying further remotely from the pipe outer surface, the scanning probes are embodied as giant magnetoresistance sensors.

11. The device of any one of claims 7-9, wherein the scanning probe is embodied as a giant magnetoresistance sensor for the additional detection of the vertical field component of the magnetic stray flux.

12. The device of any one of claims 7-9, wherein the scanning probe is embodied as a Hall probe for the additional detection of the vertical field component of the magnetic stray flux.

13. The device of any one of claims 7-9, wherein the scanning probe is embodied as an induction coil for the additional detection of the vertical field component of the magnetic stray flux.

* * * * *